United States Patent [19]
Lemanski et al.

[11] Patent Number: 6,156,942
[45] Date of Patent: Dec. 5, 2000

[54] CATALYST STABILIZING ADDITIVE IN THE HYDROLYSIS OF ALKYLENE OXIDES

[75] Inventors: Michael Francis Lemanski, Houston, Tex.; Eugene Marie Godfried Andre Van Kruchten, Amsterdam, Netherlands; Robert Kunin, Trenton, N.J.

[73] Assignee: Shell Oil Company, Houston, Tex.

[21] Appl. No.: 09/211,387

[22] Filed: Dec. 14, 1998

[51] Int. Cl.[7] .................................................. C07C 27/00
[52] U.S. Cl. ............................................................ 568/867
[58] Field of Search ............................................. 568/867

[56] References Cited

U.S. PATENT DOCUMENTS

| | | | |
|---|---|---|---|
| 2,409,441 | 10/1946 | Metzger | 568/867 |
| 4,393,254 | 7/1983 | Johnson, Jr. et al. | |
| 4,560,813 | 12/1985 | Collier | 568/867 |
| 4,579,983 | 4/1986 | Keen. | |
| 4,701,571 | 10/1987 | Soo | 568/867 |
| 5,488,184 | 1/1996 | Reman | 568/867 |

FOREIGN PATENT DOCUMENTS

95/20559  3/1995  WIPO.

OTHER PUBLICATIONS

International Search Reports dated Feb. 24, 2000.

*Primary Examiner*—Michael L. Shippen

[57] ABSTRACT

A process for the preparation of an alkylene glycol by reacting an alkylene oxide with water in the presence of a solid catalytic composition which includes a strongly basic ion exchange resin coordinated with one or more anions, and a stabilising additive which is an acidic ion exchange resin. Preferably the acidic ion exchange resin is of the weakly acidic methacrylate type.

9 Claims, No Drawings

CATALYST STABILIZING ADDITIVE IN THE HYDROLYSIS OF ALKYLENE OXIDES

FIELD OF THE INVENTION

The present invention relates to a process for the preparation of an alkylene glycol by reacting an alkylene oxide with water in the presence of a catalytic composition.

BACKGROUND OF THE INVENTION

Alkylene glycols, in particular monoalkylene glycols, are of established commercial interest. For example, monoalkylene glycols are being used in anti-freeze compositions, as solvents and as base materials in the production of polyalkylene terephthalates e.g. for fibres or bottles.

The production of alkylene glycols by liquid phase hydrolysis of alkylene oxide is known. The hydrolysis is performed without a catalyst by adding a large excess of water, e.g. 20 to 25 moles of water per mole of alkylene oxide, or it is performed with a smaller excess of water in a catalytic system. The reaction is considered to be a nucleophilic substitution reaction, whereby opening of the alkylene oxide ring occurs, water acting as the nucleophile. Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative for increasing the reaction selectivity without having to use a large excess of water. Usually these efforts have focused on the selection of more active hydrolysis catalysts and various catalysts have been disclosed.

Both acid and alkaline hydrolysis catalysts have been investigated, whereby it would appear that the use of acid catalysts enhances the reaction rate without significantly affecting the selectivity, whereas by using alkaline catalysts generally lower selectivities with respect to the monoalkylene glycol are obtained.

Certain anions, e.g. bicarbonate (hydrogen carbonate), bisulphite (hydrogen sulphite), formate and molybdate, are known to exhibit good catalytic activity in terms of alkylene oxide conversion and selectivity towards monoalkylene glycol. However when the salts of these anions are used as the catalyst in a homogeneous system, work-up of the reaction product by distillation will pose a problem because the salts are poorly soluble in the glycol and tend to make it semi-solid. Quaternary ammonium salts remain soluble in the glycol reaction product.

High conversions, good selectivity and a low water/alkylene oxide ratio can be obtained with the process, disclosed in EP-A 0 156 449 and EP-A 0 160 330 (both of Union Carbide). According to these documents the hydrolysis of alkylene oxides is carried out in the presence of a selectivity-enhancing metalate anion-containing material, preferably a solid having electropositive complexing sites having affinity for the metalate anions. The said solid is preferably an anion exchange resin, in particular a styrene-divinyl benzene copolymer. The electropositive complexing sites are in particular quaternary ammonium, protonated tertiary amine or quaternary phosphonium. The metalate anions are specified as molybdate, tungstate, metavanadate, hydrogen pyrovanadate and pyrovanadate anions. A complication of this process is that the alkylene glycol-containing product stream also comprises a substantial amount of metalate anions, displaced from the electropositive complexing sites of the solid metalate anion containing material. In order to reduce the amount of metalate anions in the alkylene glycol product stream, this stream is contacted with a solid having electropositive complexing sites associated with anions which are replaceable by the said metalate anions.

In WO 95/20559 (Shell) there is disclosed a process for the preparation of alkylene glycols wherein an alkylene oxide is reacted with water in the presence of a catalyst composition comprising a solid material having one or more electropositive sites, which are coordinated with one or more anions other than metalate or halogen anions, e.g. bicarbonate, bisulphite and carboxylate, with the proviso that when the solid material is an anionic exchange resin of the quaternary ammonium type and the anion is bicarbonate the process is performed in the substantial absence of carbon dioxide. According to this document, the presence of carbon dioxide in the feed is detrimental to the catalytic effect of bicarbonate-exchanged resins of the quaternary ammonium type.

A drawback shared by the conventional anionic exchange resins is their limited tolerance to heat. In practising the process of alkylene oxide hydrolysis according to WO 95/20559 with catalyst compositions based on conventional organic quaternary ammonium ion exchangers it has been found, that under severe alkylene oxide hydrolysis reaction conditions (high temperature and/or long service) the catalytic activity (selectivity and/or conversion) of the conventional resin-based catalysts tends to deteriorate. Moreover, under these reaction conditions these catalysts were found to undergo swelling.

The sensitivity to heat of anionic exchange resins has been known for a long time. According to Elizabeth W. Baumann, in J. of Chemical and Engineering Data 5 (1960) 376–382, the degradation of AMBERLITE IRA-400 which is a strong base (quaternary ammonium) ion exchange resin having three methyl groups in its quaternary structure can (according to two decomposition reactions 1a and 1b) liberate trimethylamine which can be absorbed by a cation exchange resin such as AMBERLITE IR-120-H, if present, or methanol which is not absorbed by the cation exchange resin. In the first column of the article it is further remarked, that "the presence of this resin [AMBERLITE IR-120-H] provides a means for absorbing basic decomposition products that might affect the progress of decomposition, permits study of the decomposition by reaction 1a and roughly duplicates the conditions in a mixed bed deionization system". The article contains no showing of any effect of AMBERLITE IR-120-H, which is a strongly acidic ion exchange resin of the sulphonic type, on the thermal stability of the anionic exchange resin. And of course the article is not concerned with the stability of any catalytic effect associated with an ionic exchange resin.

In U.S. Pat. No. 4,579,983 (Union Carbide) there is disclosed a process for making alkylene glycols from alkylene oxide and water in the presence of a water-insoluble phase containing a selectivity-enhancing organometalate which may comprise an anion exchange resin, and a stabilising material which is water-soluble and comprises a cation and a selectivity-enhancing metalate anion. This stabilising material is thus a metalate salt.

In the co-pending European Patent Application No. ........., filed on even day herewith, there is disclosed a process for the preparation of alkylene glycols by reacting an alkylene oxide with water in the presence of a catalyst composition including a carboxylic acid derivative, having in its chain molecule one or more carboxyl groups and one or more carboxylate groups, the individual carboxyl and/or carboxylate groups being separated from each other in the chain molecule by a separating group consisting of at least one atom. Catalysts compositions including such carboxylic acid derivatives immobilised on a solid support, in particular an anionic exchange resin, are specifically claimed. One advantage of the carboxylic acid derivatives as defined in this application is that their catalytic combination with anionic exchange resins is more stable.

It has now been found that the stability of solid catalysts in the conversion of alkylene oxide to alkylene glycol, which solid catalysts include a strongly basic ion exchange resin coordinated with one or more anions, can be considerably enhanced by adding a relatively small amount of an acidic ion exchange resin.

SUMMARY OF THE INVENTION

The present invention relates to a process for the preparation of an alkylene glycol by reacting an alkylene oxide with water in the presence of a solid catalytic composition which includes a strongly basic ion exchange resin coordinated with one or more anions, and a stabilising additive which is an acidic ion exchange resin.

The present invention further relates to a solid catalytic composition for use in the preparation of an alkylene glycol by reacting an alkylene oxide with water, which includes a strongly basic ion exchange resin coordinated with one or more anions, and a stabilising additive which is an acidic ion exchange resin.

DETAILED DESCRIPTION OF THE INVENTION

As such, the solid catalytic compositions as herein defined are effective as alkylene oxide hydrolysis catalysts in a heterogeneous liquid reaction system. Compared to catalytic compositions having the same components without the acidic ion exchange resin, the compositions according to the present invention are more stable and retain their selectivity and stability under severe reaction conditions as well as being more resistant to swelling.

Any of a large number of strongly basic anion exchange resins (IER's) can be used as the solid support for the catalytic anion, in particular those wherein the basic groups are quaternary ammonium or quaternary phosphonium groups. IER's based on vinylpyridine and IER's based on polysiloxanes can also be used.

Strongly basic anionic exchange resins which are suitable for use are known per se and many are commercially available, e.g. the ones sold under the trade names AMBERJET 4200, AMBERLITE 400, IRA 404, LEWATIT M 500WS, DOWEX 1*8, DOWEX MSA-1 (all of which are products based on polystyrene, cross-linked with divinylbenzene) and Reillex HPQ (based on polyvinylpyridine, cross-linked with divinylbenzene).

The catalytic anion which is coordinated with the anion exchange resin can advantageously be chosen from the group of metalates such as molybdate, tungstate and vanadate, carboxylates such as formate and citrate, bicarbonate and bisulphite. Particularly advantageous are the polycarboxylates, having in their chain molecule one or more carboxyl groups and one or more carboxylate groups, the individual carboxyl and/or carboxylate groups being separated from each other in the chain molecule by a separating group consisting of at least one atom. Of the polycarboxylates, citrate is most preferred.

There are three types of acidic ion exchange resins, i.e. the strongly acidic ion exchange resins of the sulphonic type, the acidic ion exchange resins of the acrylate type and the weakly acidic ion exchange resins of the methacrylate type. For the purpose of the present invention, the overall acidic function should be kept relatively low because otherwise the selectivity of the catalytic composition can be adversely affected. Therefore a weakly acidic ion exchange resin, i.e. one of the methacrylate type, is best suited. However, it will be understood that a small amount of one or both of the two other types, either alone or in combination with the methacrylate type, is also within the scope of the present invention.

Examples of commercially available weakly acidic ion exchange resins of the methacrylate type are those known by the trade marks AMBERLITE IRC-50, AMBERLITE GC-50, AMBERLITE IRP-64 and AMBERLITE IRP-88.

Examples of commercially available acidic ion exchange resins of the acrylate type are those known by the trade marks AMBERLITE IRC-86, AMBERLITE IRC-76, IMAC HP 336 and LEWATIT CNP 80.

Examples of commercially available strongly acidic ion exchange resins of the sulphonic type are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT S 100 MB and LEWATIT S 100 G1.

In terms of exchange capacity or equivalent of active sites, the relative amount of acidic ion exchange resin to be used according to the present invention is generally from 10 to 200%, based on the total capacity of the strongly basic ion exchange resin. Preferably this amount is from 15 to 100%, more preferably from 20 to 50%.

In terms of weight, the relative amount of acidic ion exchange resin to be used according to the present invention is generally from 5 to 70 wt % of the basic (anionic) exchange resin. Preferably the amount is from 5 to 50 wt %, more preferably from 10 to 30 wt %.

Preferably the two components, i.e. the strongly basic ion exchange resin which is coordinated with one or more catalytically effective anions, and the stabilising additive which is a acidic ion exchange resin, are used in intimate admixture.

The coordination of the strongly basic ion exchange resin with the catalytically effective anion can in principle be performed before or after admixing with the stabilising additive. Preferably the coordination is performed before admixing.

The alkylene oxides used as starting material in the process of the invention have their conventional definition, i.e. they are compounds having a vicinal oxide (epoxy) group in their molecules.

Particularly suitable are alkylene oxides of the general formula

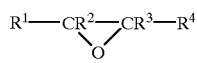

wherein $R^1$ to $R^4$ independently represent a hydrogen atom or an, optionally substituted, alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$–$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane, 2,3-epoxybutane and glycidol. Ethylene oxide and propylene oxide are of particular commercial importance.

As mentioned above, it is advantageous to perform the hydrolysis of the alkylene oxides, without using excessive amounts of water. In the process according to the present invention, amounts of water in the range of 1 to 15 moles per mole of alkylene oxide are quite suitable, amounts in the range of 1 to 6 on the same basis being preferred. In the process of the invention high selectivities with respect to the mono-alkylene glycol are often already achieved, when only 4 or 5 moles of water per mole of alkylene oxide are supplied.

The process of the invention may be carried out in batch operation. However, in particular for large scale embodiments it is preferred to operate the process continuously.

Such continuous process can be carried out in a fixed bed reactor, operated in up-flow or down-flow. Down-flow operation is preferred. Under certain chosen circumstances the catalytic conversion of EO may be incomplete, in which situation rest EO can be thermally hydrolysed in the dead space of the reactor below the catalyst bed. Since this thermal hydrolysis is less specific towards MEG, it is recommended to minimise the liquid hold-up in the reactor. This can be achieved by filling the reactor outlet part with internals or inert packing material to reduce its volume, and/or by adding an inert gas, such as nitrogen, to the reactor feed mixture and operating the reactor under so-called trickle flow conditions.

In order to obtain adequate time-yield values, it is recommended to perform the process under elevated temperature and pressure conditions.

Suitable reaction temperatures are generally in the range from 80 to 200° C., whereby temperatures in the range from 90 to 150° C. are preferred. The reaction pressure is usually selected in the range of 200 to 3000, preferably 200 to 2000 kPa. For batch operations of the process, the selected reaction pressure is advantageously obtained by pressurising with an inert gas, such as nitrogen. If desired, mixtures of gases may be used, for example a mixture of carbon dioxide and nitrogen is in certain instances advantageous.

In order to accommodate any swelling of the catalyst during operation, the reactor volume can advantageously be greater than the volume occupied by of the catalyst therein, for example 10 to 70 vol % greater.

The following Examples will illustrate the invention.

EXAMPLES

I. Catalyst Preparation

I.1 Two strongly basic ion exchange resins of the quaternary ammonium type were used:

AMBERJET 4200, a mono-disperse cross-linked polystyrene/divinylbenzene based resin ex Rohm and Haas, chloride form, exchange capacity 1.4 meq/ml;

AMBERLITE IRA-404, a cross-linked polystyrene/divinylbenzene based resin ex Rohm and Haas, chloride form, exchange capacity 1.05 meq/ml.

I.2 The resin was treated as follows to immobilise the catalytically active anion (bicarbonate, formate, citrate mono-anion) on the resin:

150 ml of wet resin was slurried in a water filled glass tube (60×2.5 cm);

chloride was exchanged by treatment with sodium bicarbonate, sodium formate or monosodium citrate in each case in aqueous solution (10 molar excess, in 2500 g of water) for approximately 5 hours (LHSV: 4 l/l.h);

the exchanged resin was washed with 1200 ml of water for 2 hours (LHSV: 4 l/l.h).

By this procedure most (>98%) of the chlorine anions in the resin were exchanged by the desired anion.

I.3 The resin was treated as follows to immobilise the catalytically active anion (molybdate) on the resin:

140 ml of wet resin was stirred gently in 2300 g of a 3% w aqueous solution of sodium molybdate ($Na_2MoO_4$) overnight at room temperature;

the resin was transferred into a vertical glass ion exchange column and then rinsed by passing water (2500 g) at room temperature through the column (LHSV: 3.4 l/l.h);

subsequently 6500 g of a 3% w aqueous sodium molybdate solution was passed through the column at room temperature (LHSV 1.7 l/l.h) and then treated with 1500 g of hot (75° C.) molybdate solution (3% w; LHSV 3.4 l/l.h)

finally, rinsing was carried out with 3000 g of hot (75° C.) water and 3000 g of water at room temperature, respectively (LHSV 3.9 l/l.h).

By this procedure most (>98%) of the chlorine anions in the resin were exchanged by the desired anion.

I.4 A weakly acidic ion exchange resin of the methacrylate type was used:

AMBERLITE IRC-50, a crosslinked polymethacrylate/divinylbenzene resin ex Rohm and Haas, hydrogen form, exchange capacity 3.25 meq/ml.

I.5 A strongly acidic ion exchange resin of the sulphonic acid type was used:

AMBERLYST 15, a crosslinked polystyrene/divinyl benzene resin ex Rohm and Haas, hydrogen form, exchange capacity 1.7 meq/ml.

I.6 The desired catalyst composition was prepared by mixing the catalyst based on the strongly basic ion exchange resin (AMBERJET 4200 type, AMBERLITE IRA-404 type) with the appropriate amount of the acidic ion exchange resin (AMBERLITE IRC-50, AMBERLYST 15).

II. Examples 1–22

Batch EO Hydrolysis

A 250 ml autoclave was filled with the catalyst (30 mmol of total catalyst, thus mmol of quaternary ammonium on AMBERJET 4200 and mmol $H^+$ on IRC-50) and water (100 g; 5.55 mol). The gascap was purged 3 times with nitrogen and an initial pressure of 1000 kPa was employed. The mixture was heated to 100° C. Ethylene oxide (44 g; 1 mol) was slowly added under stirring (500 rpm). The reaction mixture was maintained under continuous stirring for 6 hours at 100° C. An end of run sample was taken for GLC analysis.

The results (EO conversion and MEG selectivity data) are summarised in Table 1.

TABLE 1

| Example No. | Catalyst | Amount of catalyst (mmol basic/ mmol acidic) | EO conversion* (%) | Selectivity towards MEG** (mol %) |
|---|---|---|---|---|
| Comp. 1 | | —/— | 99.2 | 67.8 |
| Comp. 2 | AMBERJET 4200/$HCO_3^-$ (bicarbonate) | 30/0 | 99.0 | 88.3 |
| Comp. 3 | AMBERLYST 15 | 0/30 | 99.9 | 74.1 |
| Comp. 4 | IRC-50 | 0/30 | 99.8 | 70.5 |
| Comp. 5 | IRC-50 | 0/6 | 99.8 | 67.7 |
| 6 | AMBERJET 4200/$HCO_3^-$ + IRC-50 | 6/24 | 99.6 | 76.2 |
| 7 | AMBERJET 4200/$HCO_3^-$ + IRC-50 | 15/15 | 99.6 | 83.2 |
| 8 | AMBERJET 4200/$HCO_3^-$ + IRC-50 | 18/12 | 99.7 | 84.7 |
| 9 | AMBERJET 4200/$HCO_3^-$ + IRC-50 | 24/6 | 99.7 | 86.0 |
| 10 | AMBERJET 4200/$HCO_3^-$ + AMBERLYST 15 | 24/6 | 99.8 | 84.2 |
| Comp. 11 | AMBERJET 4200/$HCO_2^-$ (formate) | 30/0 | 99.4 | 79.3 |
| 12 | AMBERJET 4200/$HCO_2^-$ + IRC-50 | 24/6 | 99.7 | 77.7 |
| 13 | AMBERJET 4200/$HCO_2^-$ + IRC-50 | 15/15 | 99.6 | 79.6 |
| Comp. 15 | IRA-404/$HCO_2^-$ (formate) | 30/0 | 99.6 | 82.1 |
| 16 | IRA-404/$HCO_2^-$ + IRC-50 | 24/6 | 99.8 | 77.4 |
| Comp. 17 | AMBERJET 4200/citrate mono-anion | 30/0 | 99.6 | 79.9 |
| 18 | AMBERJET 4200/citrate mono-anion + IRC-50 | 24/6 | 99.5 | 79.3 |
| Comp. 19 | IRA-404/citrate mono-anion | 30/0 | 99.6 | 79.8 |
| 20 | IRA-404/citrate mono-anion + IRC-50 | 24/6 | 99.6 | 77.4 |
| Comp. 21 | AMBERJET 4200/$MoO_4^{2-}$ (molybdate) | 30/0 | 97.1 | 80.4 |
| 22 | AMBERJET 4200/$MoO_4^{2-}$ + IRC-50 | 15/15 | 96.7 | 80.1 |

*: EO conversion (mol %) = 100 × (MEG + 2 DEG + 3 TEG)/(EO + MEG + 2 DEG + 3 TEG)
**: Selectivity towards MEG (mol %) = 100 × MEG/(MEG + 2 DEG + 3 TEG)

The results in Table 1 indicate that the acidic ion exchange resins have little catalytic activity, (basis selectivity of the reaction without any addition, Example 1) but that their addition together with a basic ion-exchange based catalyst does not diminish its catalytic effect.

capacity (the sum of the two previous capacities) in the fresh and used catalyst were determined by titration and the % difference (change during use) noted.

The results are summarised in Table 2.

TABLE 2

| Example No. | Catalyst | Strongly basic capacity (mmol/g) | | | Weakly basic capacity (mmol/g) | | | Total anion capacity (mmol/g) | | |
|---|---|---|---|---|---|---|---|---|---|---|
| | | 150° C. begin | 150° C. end | % change | 150° C. begin | 150° C. end | % change | 150° C. begin | 150° C. end | % change |
| Comp. 23 t = 48 hrs | AMBERJET 4200/bicarbonate | 3.19 | 1.15 | −64 | 0.27 | 0.68 | +152 | 3.46 | 1.83 | −47 |
| 24 t = 48 hrs | AMBERJET 4200/bicarbonate + IRC-50 (24/6) | 2.26 | 1.50 | −34 | 0.11 | 0.47 | +327 | 2.37 | 1.97 | −17 |
| 25 t = 48 hrs | AMBERJET 4200/bicarbonate + AMBERLYST 15 (24/6) | 3.77 | 2.18 | −42 | 0.27 | 0.34 | +25 | 4.04 | 2.52 | −38 |
| Comp. 26 t = 168 hrs | AMBERJET 4200/formate | 3.19 | 1.02 | −68 | 0.27 | 0.39 | +44 | 3.46 | 1.41 | −59 |
| 27 t = 168 hrs | AMBERJET 4200/formate + IRC-50 (24/6) | 2.47 | 1.59 | −36 | 0.18 | 0.24 | +33 | 2.66 | 1.83 | −31 |

III. Examples 23–27

Catalyst Stability Test

The thermal stability was tested under severe conditions by placing 20 ml of the catalyst in a 65 cm long 0.5 inch wide Hoke tube, provided with a heating jacket using a hot oil system. Water was pumped with an HPLC pump with an LHSV of 1 l/l.h over the catalyst bed at 150° C. and a pressure of 1000 kPa during 48 or 168 hours. Then the catalyst sample was removed from the reactor. The strongly basic capacity (quaternary ammonium groups), the weakly basic capacity (tertiary amine groups) and the total anion The results in Table 2 indicate that in this severe accelerated stability test the strongly basic IER based catalyst in the presence of a small amount of an acidic ion exchange resin is more than 2 times more stable than the corresponding catalyst without the acidic ion exchange resin.

IV. Example 28–29

Continuous EO Hydrolysis

Example 28

AMBERJET 4200/$HCO^-$ (bicarbonate)+IRC-50 (4/1 mol/mol ratio) catalyst was used in this test, wherein process parameters were varied (water:EO molar ratio between 7.5 and 20.6; LHSV between 0.92–2.82 and maximum bed temperature between 94–124° C.).

The reactor was a 9 mm internal diameter stainless steel tube, with a hot oil heating jacket, and was loaded with 23 ml of catalyst. The EO/water feed was pumped upflow through the catalyst bed. Liquid EO was pumped to the reactor by a plunger pump (BHS-Labotron LDP-5). Before entering the catalyst bed this EO was mixed in line with water, pumped by an HPLC pump. Reaction temperature was controlled by the oil temperature. In the centre of the catalyst bed a thermowell was placed with a thermocouple to measure bed temperatures. Reactor effluent was cooled and collected in a product vessel, from which samples were taken at time intervals for GLC analysis.

The results are summarised in Table 3.1.

TABLE 3.1

Example 28

| Run-hour | $H_2O$/EO mol ratio | LHSV (1/1·h) | Max. bed temperature (° C.) | EO conversion (%)* | Selectivity towards MEG (mol %)** |
|---|---|---|---|---|---|
| 0 | 8 | 0.92 | 112 | 100 | 97.2 |
| 17 | 8.6 | 0.97 | 105 | 99.9 | 97.2 |
| 42 | 7.5 | 0.93 | 105 | 99.9 | 97.3 |
| 47 | 18.9 | 0.97 | 94 | 99.7 | 98.5 |
| 64 | 18.9 | 0.97 | 94 | 99.8 | 98.7 |
| 70 | 4.8 | 0.94 | 114 | 99.2 | 95.6 |
| 137 | 7.8 | 0.92 | 104 | 99.8 | 97.3 |
| 142 | 7.8 | 1.83 | 113 | 95.2 | 97.2 |
| 163 | 7.9 | 2.82 | 124 | 92.1 | 97.2 |
| 186 | 8.0 | 0.92 | 102 | 99.8 | 97.0 |
| 210 | 20.6 | 1.0 | 100 | 100 | 98.8 |
| 305 | 8.0 | 0.93 | 101 | 99.7 | 97.1 |
| 354 | 8.0 | 0.93 | 105 | 99.9 | 96.3 |
| 401 | 8.0 | 0.92 | 105 | 99.9 | 96.5 |
| 473 | 7.8 | 0.92 | 103 | 99.8 | 96.9 |
| 520 | 7.7 | 0.92 | 100 | 99.9 | 96.7 |
| 641 | 7.8 | 0.92 | 100 | 99.9 | 96.8 |
| 690 | 7.8 | 0.92 | 100 | 99.9 | 96.4 |

*: EO conversion (mol %) = 100 × (MEG + 2 DEG + 3 TEG)/(EO + MEG + 2 DEG + 3 TEG)
**: Selectivity towards MEG (mol %) = 100 × MEG/(MEG + 2 DEG + 3 TEG)

Comparative Example 29

For comparison the results of a similar test using AMBERJET 4200/bicarbonate catalyst (thus without the IRC-50 stabiliser) is presented in Table 3.2. Note that in this experiment a fixed water/EO mol ratio (7.5) is used. Comparison with the results in Table 3.1 at this mol ratio shows that the addition of IRC-50 has no detrimental effect on the selectivity to MEG in such continuous mode fixed-bed operation.

TABLE 3.2

Comparative Example 29

| Run-hour | $H_2O$/EO mol ratio | LHSV (1/1·h) | Max. bed temperature (° C.) | EO conversion (%)* | Selectivity towards MEG (mol %)** |
|---|---|---|---|---|---|
| 17 | 7.5 | 1.1 | 104 | 99.8 | 96.7 |
| 43 | 7.5 | 1.1 | 103 | 99.9 | 96.8 |
| 113 | 7.5 | 1.1 | 112 | 100.0 | 95.8 |
| 137 | 7.5 | 1.1 | 99 | 99.9 | 96.6 |
| 161 | 7.5 | 1.1 | 99 | 99.9 | 96.6 |
| 233 | 7.5 | 1.1 | 102 | 100.0 | 96.3 |
| 309 | 7.5 | 1.1 | 104 | 100.0 | 96.3 |
| 328 | 7.5 | 1.1 | 110 | 100.0 | 95.9 |
| 335 | 7.5 | 1.1 | 98 | 99.9 | 96.5 |
| 353 | 7.5 | 1.1 | 99 | 99.9 | 96.5 |

*: EO conversion (mol %) = 100 × (MEG + 2 DEG + 3 TEG)/(EO + MEG + 2 DEG + 3 TEG)
**: Selectivity towards MEG (mol %) 100 × MEG/(MEG + 2 DEG + 3 TEG)

V. Examples 30–33

Continuous EO Hydrolysis

Example 30 and Comparative Example 31

AMBERJET 4200/formate+IRC-50 catalyst (4/1 mol/mol ratio; Example 30) was used in a continuous fixed-bed experiment. The long-time performance was compared with that of AMBERJET 4200/formate (Comparative Example 31) under exactly identical process conditions.

The experiments were carried out in a once-through mode. The 24 cm long reactor consisted of a 20 mm (inner diameter) wide glass tube in a 34 mm wide stainless steel metal pipe. Between the glass reactor tube and the SS outer tube a Teflon (PTFE) layer was used as an insulator. An electrical heating system was used at the outer SS tube to compensate for heat losses; the temperature set point for this heating device was set at the temperature of the water/EO reactor feed. The reactor was charged with 60 ml of catalyst. The water feed was preheated to achieve the desired reactor inlet temperature prior to mixing with EO. The temperature of the feed was measured using a thermocouple placed on top of the reactor and the outlet temperature was measured using a thermocouple just below the catalyst bed in the reactor outlet.

The process conditions during these experiments are compiled in Table 4.1.

TABLE 4.1

| Pressure (kPa) | 1000 |
| Reactor inlet temperature (° C.) | 65–90 |
| Reactor outlet temperature (° C.) | 85–110 |
| $H_2O$/EO flow (ml/h) | 130–150 |
| Mol ratio $H_2O$/EO (mol/mol) | 10–25 |
| LHSV (l/l.h) | 2.3–2.5 |

In each Example the reaction was run until cut-off when catalyst swelling resulted in a volume increase of 55 vol %. This volume increase was reached by the 2347th run-hour in Comparative Example 31, but only by the 4037th run-hour in Example 30 which is according to the present invention.

The EO conversion and selectivity towards MEG were followed in each Example until the cut-off at 55 vol % swelling of the respective catalyst. The results are compiled in Table 4.2 and 4.3, showing that the addition of IRC-50 to the AMBERJET 4200/formate catalyst had no significant effect on the catalytic performance in terms of EO conversion and MEG selectivity under the process conditions.

TABLE 4.2

Example 30

| Run hour (h) | EO conversion (mol %) | Selectivity towards MEG (mol %) |
|---|---|---|
| 192 | 98.3 | 98.7 |
| 288 | 99.9 | 98.6 |
| 480 | 98.7 | 99.0 |
| 752 | 98.6 | 98.7 |
| 848 | 98.1 | 98.8 |
| 1750 | 95.6 | 98.4 |
| 2019 | 96.9 | 96.4 |
| 2424 | 97.6 | 96.1 |
| 2874 | 96.4 | 98.4 |
| 3194 | 96.1 | 98.1 |
| 3352 | 96.2 | 97.0 |
| 3769 | 96.4 | 96.9 |
| 4007 | 96.2 | 98.3 |

TABLE 4.3

Comparative Example 31

| Run hour (h) | EO conversion (mol %) | MEG selectivity (mol %) |
|---|---|---|
| 198 | 99.6 | 98.6 |
| 295 | 99.7 | 98.6 |
| 494 | 99.9 | 98.6 |
| 740 | 99.9 | 98.0 |
| 833 | 99.7 | 97.8 |
| 1750 | 99.8 | 96.1 |
| 2015 | 98.7 | 96.8 |

Example 32 and Comparative Example 33

AMBERJET 4200/citrate mono-anion+IRC-50 catalyst and AMBERJET 4200/citrate mono-anion were compared (Example 32 and Comparative Example 33 respectively) in long-time experiments under the same conditions as in Examples 30 and 31.

In each Example the reaction was run until cut-off when catalyst swelling resulted in a volume increase of 55 vol %. This volume increase was reached by the 2645th run-hour in Comparative Example 32, but only by the 3246th run-hour in Example 33 which is according to the present invention.

The EO conversion and selectivity towards MEG were followed in each Example until the cut-off at 55 vol % swelling of the respective catalyst. The results are compiled in Table 5.1 and 5.2, showing that the addition of IRC-50 to the AMBERJET 4200/citrate catalyst had no significant effect on the catalytic performance in terms of EO conversion and MEG selectivity under the process conditions.

TABLE 5.1

Example 32

| Run hour (h) | EO conversion (mol %) | Selectivity towards MEG (mol %) |
|---|---|---|
| 73 | 99.5 | 98.4 |
| 407 | 99.7 | 98.5 |
| 677 | 99.5 | 98.7 |
| 744 | 99.3 | 98.6 |
| 1013 | 99.8 | 98.7 |

TABLE 5.1-continued

Example 32

| Run hour (h) | EO conversion (mol %) | Selectivity towards MEG (mol %) |
|---|---|---|
| 1247 | 98.7 | 97.7 |
| 1346 | 99.1 | 97.8 |
| 1416 | 99.2 | 97.8 |
| 1584 | 99.6 | 97.7 |
| 1852 | 99.5 | 97.8 |
| 1972 | 98.6 | 98.1 |
| 2189 | 99.0 | 97.1 |
| 2357 | 98.9 | 97.1 |
| 2525 | 99.3 | 97.1 |
| 2808 | 96.7 | 96.7 |
| 3144 | 97.7 | 97.3 |

TABLE 5.2

Example 41

| Run hour (h) | EO conversion (mol %) | Selectivity towards MEG (mol %) |
|---|---|---|
| 90 | 99.9 | 98.3 |
| 425 | 99.9 | 98.7 |
| 670 | 99.8 | 98.6 |
| 750 | 99.9 | 98.6 |
| 1000 | 99.7 | 98.6 |
| 1238 | 99.9 | 98.2 |
| 1406 | 99.7 | 97.8 |
| 1622 | 99.7 | 97.8 |
| 1745 | 99.6 | 97.8 |
| 1895 | 99.6 | 97.0 |
| 1944 | 99.6 | 97.3 |
| 2060 | 99.4 | 96.9 |
| 2350 | 99.3 | 97.1 |
| 2517 | 98.9 | 97.2 |

What is claimed is:

1. A process for the preparation of an alkylene glycol by reacting an alkylene oxide with water in the presence of a solid catalytic composition which includes a strongly basic ion exchange resin coordinated with one or more anions, and a stabilising additive which is an acidic ion exchange resin.

2. A process according to claim 1, characterised in that the acidic ion exchange resin is of the weakly acidic methacrylate type.

3. A process according to claim 1, characterised in that the strongly basic ion exchange resin is of the quaternary ammonium type.

4. A process according to claim 1, characterised in that the strongly basic ion exchange resin is of the quaternary phosphonium type.

5. A process according to claim 1, characterised in that in terms of exchange capacity or equivalent of active sites, the relative amount of acidic ion exchange resin is from 10 to 200%, based on the total capacity of the strongly basic ion exchange resin.

6. A process according to claim 1, characterised in that the anion is chosen from the group of metalates, carboxylates, bicarbonate and bisulphite.

7. A process according to claim 6, characterised in that the carboxylate is formate.

8. A process according to claim 6, characterised in that the carboxylate is a polycarboxylic acid derivative having in its chain molecule one or more carboxyl groups and one or more carboxylate groups, the individual carboxyl and/or carboxylate groups being separated from each other in the chain molecule by a separating group consisting of at least one atom.

9. A process according to claim 8, characterised in that the carboxylate is citrate.

* * * * *